US010821375B2

(12) United States Patent
Fonseca et al.

(10) Patent No.: US 10,821,375 B2
(45) Date of Patent: Nov. 3, 2020

(54) CONTINUOUS PRODUCTION OF PARTICLES

(71) Applicant: Hovione Scientia Limited, Cork (IE)

(72) Inventors: Tiago Fonseca, Loures (PT); Iris Duarte, Lisbon (PT); Márcio Temtem, Quinta do Conde (PT); João Vicente, Lisbon (PT)

(73) Assignee: Hovione Scientia Limited, Cork (IE)

( * ) Notice: Subject to any disclaimer, the term of this patent is extended or adjusted under 35 U.S.C. 154(b) by 24 days.

(21) Appl. No.: 15/562,823

(22) PCT Filed: Mar. 30, 2016

(86) PCT No.: PCT/GB2016/050894
§ 371 (c)(1),
(2) Date: Sep. 28, 2017

(87) PCT Pub. No.: WO2016/156841
PCT Pub. Date: Oct. 6, 2016

(65) Prior Publication Data
US 2018/0104618 A1  Apr. 19, 2018

(30) Foreign Application Priority Data

Mar. 31, 2015 (PT) .......................... 108368

(51) Int. Cl.
| | | |
|---|---|---|
| *B01D 9/00* | (2006.01) | |
| *A61K 9/14* | (2006.01) | |
| *A61K 31/56* | (2006.01) | |
| *A61K 31/55* | (2006.01) | |
| *B01D 63/00* | (2006.01) | |
| *B01D 63/08* | (2006.01) | |
| *B05B 1/02* | (2006.01) | |
| *B05B 12/14* | (2006.01) | |
| *F26B 3/12* | (2006.01) | |
| *F26B 17/10* | (2006.01) | |

(52) U.S. Cl.
CPC ............ *B01D 9/0054* (2013.01); *A61K 9/145* (2013.01); *A61K 31/55* (2013.01); *A61K 31/56* (2013.01); *B01D 9/0072* (2013.01); *B01D 63/005* (2013.01); *B01D 63/088* (2013.01); *B05B 1/02* (2013.01); *B05B 12/1445* (2013.01); *F26B 3/12* (2013.01); *F26B 17/101* (2013.01)

(58) Field of Classification Search
CPC ..... B01D 9/0054; B05B 1/02; B05B 12/1445; F26B 3/12; A61K 9/14; A61K 9/16
See application file for complete search history.

(56) References Cited

U.S. PATENT DOCUMENTS

| | | | |
|---|---|---|---|
| 7,147,806 B2 | 12/2006 | Castor | |
| 8,835,376 B2 * | 9/2014 | Shen | ........................ A61P 1/00 514/1.1 |
| 2002/0102312 A1 | 8/2002 | Tepper et al. | |
| 2003/0049323 A1 | 3/2003 | Hitt et al. | |
| 2003/0138878 A1 * | 7/2003 | Johannessen | ......... A23L 29/065 435/41 |
| 2005/0139144 A1 * | 6/2005 | Muller | ................... A61K 9/146 117/2 |
| 2009/0269250 A1 | 10/2009 | Panagiotou et al. | |

FOREIGN PATENT DOCUMENTS

| | | |
|---|---|---|
| CN | 1780670 A | 5/2006 |
| CN | 102164582 A | 8/2011 |
| EP | 2705838 A1 | 3/2014 |
| PT | 108368 | 3/2015 |
| WO | 2004096405 A1 | 11/2004 |
| WO | 20100036211 A1 | 4/2010 |
| WO | 2011131947 A2 | 10/2011 |
| WO | 2013144554 A1 | 10/2013 |
| WO | 2014108687 A1 | 7/2014 |
| WO | 2015114320 A1 | 8/2015 |
| WO | 2016016665 A1 | 2/2016 |
| WO | 2016156841 A1 | 10/2016 |

OTHER PUBLICATIONS

Cogent M1 (http://ecolabmicrotex.ru/wp-content/uploads/2015/02/MM_DS1249EN00.pdf) Feb. 2013, pp. 1-6 (Year: 2013).*
Cross Flow Filtration (https://cdn.gelifesciences.com/dmm3bwsv3/AssetStream.aspx?mediaformatid=10061&destinationid=10016&assetid=17054) Jan. 2014, pp. 1-82 (Year: 2014).*
Foreign Communication from a related application—International Search Report and Written Opinion of International Application No. PCT/GB2016/050894 dated Jun. 10, 2016, 11 pages.
Foreign Communication from a related application- International Preliminary Report on Patentability of International Application No. PCT/GB2016/050894 dated Aug. 28, 2017, 15 pages.
BETE Spray Dry Manual, 2005, 25 pages including cover and table of contents.
Chemical Engineering Design, "Equipment Selection, Specification and Design," Chapter 10, 2009, 3 pages including cover, publishing information and p. 606, Elsevier Ltd.

(Continued)

*Primary Examiner* — Andrew S Rosenthal
(74) *Attorney, Agent, or Firm* — Rodney B. Carroll; Conley Rose, P.C.

(57) ABSTRACT

The present invention discloses a method to continuously manufacture micro- and/or nanoparticles of single component particles or multi-component particles such as particulate amorphous solid dispersions or particulate co-crystals. The continuous method comprises the steps of 1. preparing a first solution comprising at least one component and at least one solvent and a second solution comprising at least one anti-solvent of the at least one component comprised in the first solution, 2. mixing said first solution and said second solution by means of microfluidization to produce a suspension by precipitation or co-precipitation, 3. feeding said suspension to a filtration system to obtain a concentrate stream, 4. feeding said concentrate stream to a spray dryer, 5. atomizing said concentrate stream using at least one atomization nozzle, 6. drying said atomized concentrate stream to obtain particles, and 7. collecting said particles. Single component particles or multi-component particles, particulate amorphous solid dispersions, particulate co-crystals and pharmaceutical compositions are also disclosed.

23 Claims, 7 Drawing Sheets

(56) References Cited

OTHER PUBLICATIONS

Gad, Shayne Cox, p. 663 of Pharmaceutical Manufacturing Handbook: Production and Processes, plus 2 pages of cover and publishing information, 2008, John Wiley and Sons Inc., Hoboken, New Jersey, USA, XP 002758248.

Hu, Jun, et al., "Continuous and scalable process for water-redispersible nanoformulation of poorly aqueous soluble APIs by antisolvent precipitation and spray-drying," International Journal of Pharmaceutics, 2011, pp. 198-204, vol. 404, Elsevier, B.V., XP 027575246.

Pereira, Rüben, et al., "Particle Engineering through Solvent Controlled Precipitation," Nov. 6, 2014, 1 page, Hovione, XP 055348239.

Pereira, R.J., et al., "Production of Itraconazole Nanocrystals through Solvent Controlled Precipitation," 2014 AAPS Annual Meeting and Exposition, Nov. 2, 2014, 1 page, Hovione PharmaScience S.A., XP 0055276623.

Porter, William W., et al, "Polymorphism in Carbamazepine Cocrystals," Crystal Growth and Design, 2008, pp. 14-16, vol. 8, No. 1, American Chemical Society.

Thorat, Alpana A., et al., "Liquid antisolvent precipitation and stabilization of nanoparticles of poorly water soluble drugs in aqueous suspensions: Recent developments and future perspective," Chemical Engineering Journal, 2012, pp. 1-34, vol. 181-182, Elsevier, B.V.

Vicente, J., et al., "From the Lab to Commercial Spray Drying—Maintaining Powder Properties across Scales," 2014 AAPS Annual Meeting and Exposition, Nov. 2, 2014, 1 page, Hovione PharmaScience S.A., XP 55276636.

Wang, In-Chun, et al., "Anti-solvent co-crystallization of carbamazepine and saccharin," International Journal of Pharmaceutics, 2013, pp. 311-322, vol. 450, Elsevier B.V.

Foreign communication from a related application—Examination Report of Indian Patent Application No. 201717035227 dated Nov. 15, 2019, 6 pages.

Foreign communication from a related application—First Office Action of Chinese Patent Application No. 201680031576.1 dated Jan. 10, 2020, with English translation, 22 pages.

Liu, Guoquan "The Downstream of Biotechnology," Jul. 1993, pp. 81-82 plus cover, 4 pages.

Foreign Communication from related application—Investigation Report of Provisional Patent Application, Application No. 108364, dated Nov. 12, 2015, 3 pages.

Thorat, Alpana et al., "Liquid antisolvent precipitation and stabilization of nanoparticles of poorly water soluble drugs in aqueous suspensions: Recent developments and future perspective," Chemical Engineering Journal, 2012, pp. 1-34, vol. 181-182, Elsevier B.V.

Shah, Navnit et al., "Development of novel microprecipitated bulk powder (MBP) technology for manufacturing stable amorphous formulations of poorly soluble drugs," International Journal of Pharmaceutics, 2012, pp. 53-60, vol. 438, Elsevier B.V.

D'Addio, Suzanne M. et al., "Controlling drug nanoparticle formation by rapid precipitation," Advanced Drug Delivery Reviews, 2011, pp. 417-426, vol. 63, Elsevier B.V.

Wang, In-Chun, et al., "Anti-solvent co-crystallization of carbamazepine and saccharin," International Journal of Pharmaceutics, 2013, pp. 311-322, vol. 450, Elsevier B.V.

Zhang, Hai-Xia et al., "Micronization of atorvastatin calcium by anti-solvent precipitation process", International Journalof Pharmaceutics, 2009, pp. 106-113, vol. 374, Elsevier B.V.

Chan, Hak-Kim et al., "Production methods for nanodrug particles using the bottom-up approach," Advanced Drug Delivery Reviews, 2011, pp. 406-416, vol. 63, Elsevier B.V.

Foreign communication from a related application—Office Action of Australian Patent Application No. 2016240294 dated Jul. 6, 2020, 6 pages.

\* cited by examiner

CONTINUOUS PRODUCTION OF PARTICLES

CROSS REFERENCE TO RELATED APPLICATIONS

This application is a filing under 35 U.S.C. 371 of International Application No. PCT/GB2016/050894 filed Mar. 30, 2016, entitled "Continuous Production of Particles" which claims priority to Portuguese Patent Application No. 108368 filed Mar. 31, 2015, which applications are incorporated by reference herein in their entirety.

FIELD OF INVENTION

The present invention discloses a continuous approach to designing particles of Active Pharmaceutical Ingredients (APIs), excipients or combinations of APIs and excipients (e.g. co-crystals and amorphous solid dispersions). The present invention uses controlled precipitation to promote molecular contact and/or interaction between solvent and anti-solvent streams. Moreover, the present invention discloses a continuous separation method through the combination of a filtration unit and a spray dryer. The filtration system is designed to increase the solid concentration and consequently the method's productivity, making the present invention applicable for large scale production. The present invention is in the technical field of methods to produce single component or multi-component particles (e.g. co-crystals and amorphous solid dispersions) in amorphous or crystalline form, with particle sizes in the micro- and/or nano-range.

BACKGROUND OF INVENTION

Current pharmaceutical pipelines are highly populated with new molecules presenting poor physicochemical properties, which typically translate into solubility issues. Poor solubility is one of the major concerns in the oral-drug delivery field, mainly because it limits bioavailability. It is known by those skilled in the art that the dissolution rate may be enhanced by increasing the surface area of the particles through size reduction.

Most particle size reduction methods rely on a top-down approach, where larger particles are mechanically processed. In these methods particle size is reduced by impact which can introduce impurities and limits the flexibility in controlling particle morphology. The current art comprises several techniques to reduce particle size, such as jet milling, microfluidization, high shear mixing and ball milling methods. In the case of wet methods, the suspended and processed particles may then be dried using a known method to obtain a powder.

WO 2011/131947 discloses a "top-down" approach were the target particle size is achieved following a multi steps approach. First, the API is suspended in a solvent in which it is insoluble, next the size of the API particles are reduced by cavitation and then, preferably, the particles are dried by spray drying to obtain the product as a dry powder (this method is referred to by its inventors as "Wet Polishing").

In the field of top-down technologies, the state of the art includes some examples of using membranes followed by spray drying. WO 2013/144554 discloses a method for producing particles having a reduced particle size distribution. The method disclosed comprises subjecting a suspension of particles of APIs, drug product intermediates, excipients or drug products to a size reduction step or to a size growth step and feeding said particles to a membrane separation system to separate said particles according to size. Any particles that do not meet the size criteria (permeate stream) are recycled to the size reduction step or to a size growth step. Particles that meet the size criteria (filtrate stream) may be isolated by spray drying.

However, milling API particles to submicron size is extremely challenging with top-down methods. These methods are time and energy consuming, and consequently prone to producing amorphous API domains, making it difficult to control the crystalline form and API stability.

Alternative particle size reduction methods include bottom-up approaches in which control of particle properties (particle size, density, morphology, polymorphic form, crystallinity, etc.) is achieved by starting at the molecular level with the components in solution. An example is liquid anti-solvent precipitation, which uses a suitable solvent/anti-solvent system to enable particle formation through crystallization and/or precipitation. Liquid anti-solvent precipitation has been used in the production of API-only particles, co-crystals or amorphous solid dispersions.

The state of the art includes several methods to control liquid anti-solvent precipitation for pharmaceutical compounds or intermediates. Chan et al. (*Advanced Drug Delivery Reviews*, 2011, 63, 406-416), D'Addio et al. (*Advanced Drug Delivery Reviews*, 2011, 63, 417-426) and Thorat et al. (*Chemical Engineering Journal*, 2012, 181-182, 1-34) disclosed the use of confined liquid impinging jets, multi-inlet vortex mixers, supercritical fluid technologies, ultrasound or static mixers to control supersaturation and precipitation. However, some of these technologies introduce scale-up challenges relevant to large scale production. Several downstream processes to remove the solvent used in liquid anti-solvent precipitation are also discussed by the authors of these articles, processes like spray drying, freeze drying or filtration. For example, Thorat et al. reports that the removal of solvents at large production scale is a challenge. This is mainly due to the large quantity of anti-solvent needed.

Zhang et al. (*International Journal of Pharmaceutics*, 2011, 63, 106-113) reported the production of amorphous atorvastatin calcium by liquid anti-solvent precipitation and spray drying processes. The method described comprises the preparation of a methanol solution with atorvastatin calcium followed by filtration in order to remove particulate impurities. Hydroxypropylmethylcellulose is dissolved in water and used as an anti-solvent. Both solvent and anti-solvent streams are mixed under stirring producing a suspension, which is then fed to a laboratory spray dryer. Shah et al. (*International Journal of Pharmaceutics*, 2012, 438, 53-60) also disclose a similar method to produce amorphous solid dispersions of poorly soluble compounds that cannot be processed by traditional approaches such as spray drying and hot melt extrusion. The reported method comprises the preparation of a solution of an API and an ionic polymer followed by co-precipitation into aqueous medium. The solvent is extracted by washing and the co-precipitate is isolated by filtration followed by drying in a forced air oven or fluid bed dryer. Wang et al. (*International Journal of Pharmaceutics*, 2013, 450, 311-322) reported the production of carbamazepine-saccharin co-crystals by the anti-solvent addition of a solution containing the API and the co-former under continuous stirring. The solution was filtered and dried in order to isolate the product. Although the above-mentioned methods are suitable to produce and isolate multi-compound particles in amorphous and crystal form, they are limited by the lack of control of the mixing of solvent and anti-solvent, and consequently the lack of control of particle growth and size. Moreover, it is known by those skilled in the art that the full filtration of a suspension produces a cake and promotes particle agglomeration and consequently the creation of lumps. Therefore, methods comprising the full filtration of a suspension are problematic.

The present invention provides a new continuous manufacturing method that makes use of a microreaction technology to control precipitation. The benefits of this technology include the ability to achieve homogeneous and rapid mixing of two or more fluids, thus enabling the control of particle properties (e.g. particle size, density, morphology, polymorphic form, crystallinity, etc.).

In the field of microreaction technology, the state of the art includes several examples related with particle engineering. US 2009/0269250 discloses an apparatus that facilitates molecular contact and interaction within a defined reaction chamber. With this method the inventors were able to produce a nanosuspension of norfloxacin with a particle size in the submicron range. In the apparatus of US 2009/0269250, solvent and anti-solvent are fed into an intensifier pump separately at a controlled rate in order to supply the microreaction chambers and produce the nanosuspension. One of the challenges associated with this method is the fact that after the precipitation is complete, given the ratios between solvent and anti-solvent, the solids concentration is low, resulting in costly isolation processes. In addition, WO 2016/016665 discloses a bottom-up approach to producing amorphous nanoparticles through solvent controlled precipitation using microreaction technology. This approach also results in a low solids concentration after precipitation.

Typical methods of stabilizing particles in suspension include the addition of surfactants to the suspension. However, such an approach is not always effective or recommended because of the impact surfactants can have on product quality. The present invention aims to circumvent the drawbacks associates with the addition of surfactants by using a new configuration, minimizing the aging, targeting the continuous production of particles, followed by the immediate isolation of the particles. The present invention describes a continuous separation approach overcoming the challenges with intermediate stability of the amorphous materials and reducing the need for large quantities of excipients being used to stabilize the produced materials.

The present invention provides a new approach to address the challenges associated with the prior art by:
i) providing a new approach to separation during the isolation of materials produced by precipitation or co-precipitation;
ii) enabling better control of particle characteristics;
iii) reducing the use of surfactant in formulations,
iv) supporting the continuous production of API-only particles, excipient particles or particles comprising combinations of APIs and excipients (e.g. co-crystals or amorphous solid dispersions) with particle sizes in the micro- and/or nano-range, and
v) being scalable to large scale production.

SUMMARY OF THE INVENTION

According to one aspect of the present invention, there is provided a method to continuously manufacture single component particles and or multi-component particles comprising the steps of:
preparing a first solution comprising at least one component and at least one solvent, and a second solution comprising at least one anti-solvent of the at least one component comprised in the first solution;
mixing the said first solution and said second solution by means of microfluidization or a microreaction to produce a suspension by precipitation or co-precipitation;
feeding said suspension to a filtration system to obtain a concentrate stream;
feeding said concentrate stream to a spray dryer;
atomizing the said concentrate stream using an at least one atomization nozzle;
drying the said droplets atomized concentrate stream to obtain particles; and
collecting said particles.

Other aspects of the invention relate to single component particles, multi-component particles, particulate amorphous solid dispersions and particulate co-crystals obtainable by the method of the present invention, and pharmaceutical compositions comprising said single component particles, multi-component particles, particulate amorphous solid dispersions and particulate co-crystals.

DETAILED DESCRIPTION OF THE INVENTION

Figure 1:
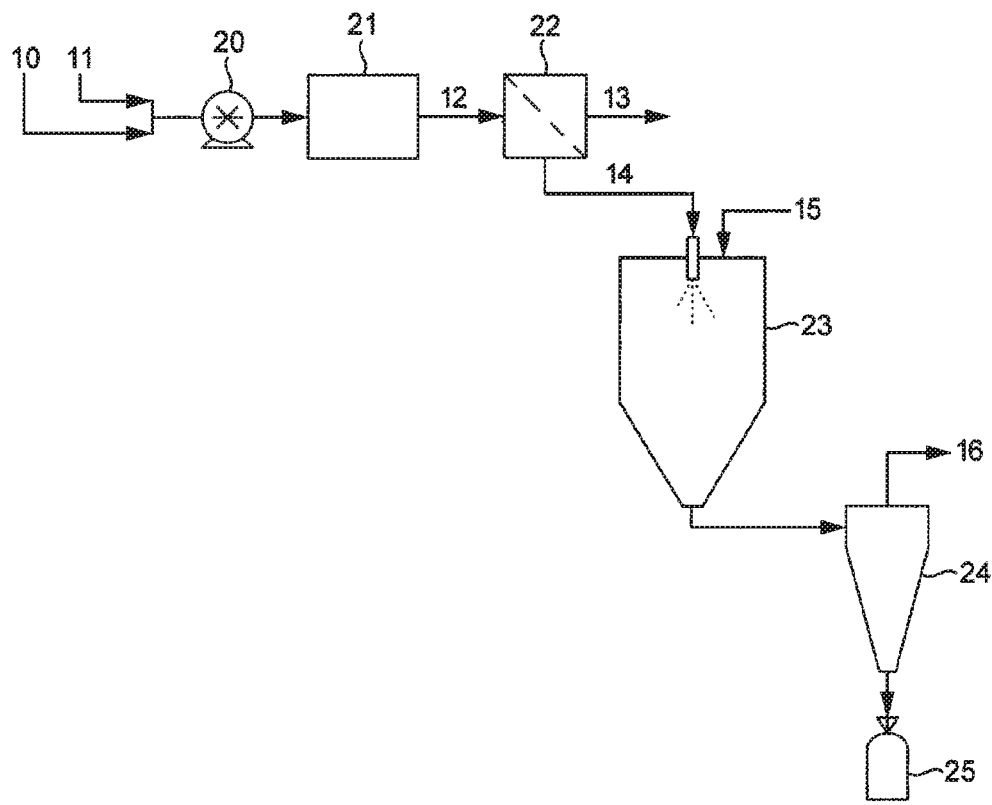
FIG. 1 is a diagram of one embodiment of the method of the present invention.

Although prior art methods to produce particles with particle sizes in the micro- and/or nano-range had already had already combined liquid anti-solvent precipitation and spray drying (see Zhang et al. discussed above), these two method steps were operated as batch processes. Combining liquid anti-solvent precipitation and spray drying in the form of a continuous process is complex because of differences in throughput at the same scale. For instance, at laboratory scale, a microreactor being used for liquid anti-solvent precipitation may have a throughput of 20-30 kg/h and yet a spray dryer may have a throughput of about 1 kg/h.

In addition, running a spray dryer directly from liquid anti-solvent precipitation decreases cyclone efficiency and consequently process yield due to the low solid loading at the cyclone inlet resulting from the low solid content in the suspension resulting from liquid anti-solvent precipitation. The inventors of the present invention overcame this problem by feeding the suspension to a filtration system to obtain a concentrate stream before feeding the concentrate stream to a spray dryer. However, adding an additional step to a method for producing particles with particle sizes in the micro- and/or nano-range is counterintuitive since adding an additional step increases residence time, which would be expected to increase particle size.

Therefore, the inventors of the present invention had to overcome technical challenges to arrive at the continuous method of the present invention.

Compared to prior art methods, the advantages of the present invention include:
- The conditions (e.g. mixing energy, solvent/anti-solvent ratio) can be manipulated to achieve the desired particle properties (e.g. particle size, density, morphology, polymorphic form, crystallinity, etc.). In particular, the conditions of the precipitation step help determine the product formed and the properties of the collected particles.
- The suspended particles obtained are either consistently in a crystalline solid state, for example in the case of an API-only particle or a co-crystal, or consistently in an amorphous solid state, for example in the case of an amorphous solid dispersion.
- The particle size of the particles obtained is within the micro- and/or nano-range, avoiding sequential processing that can lead to solid-state changes (e.g. milling).
- The method includes a concentration step to increase the solid percentage, decreasing the costs and energy requirements during isolation.
- The isolation of the particles is performed by spray drying, thus helping to prevent changes in the properties of the particles.
- The shape and morphology of the particles can further be controlled through drying process parameters, such as the temperature profile used.
- The control of the particle size in the micro- and/or nano-range can be achieved with no use or limited use of surfactants or polymers.
- The method is suitable to obtain the product in particulate form.
- The method is performed continuously.
- The method is easily scalable.

The term "amorphous solid dispersion" is defined as the dispersion of at least one API in a matrix, in the amorphous state. The matrix may comprise crystalline or amorphous polymers, surfactants or mixtures thereof.

The term "API-only" is defined as particles comprising at least one API in the absence of excipients. the API-only particles may be in crystalline or amorphous form.

The term "co-crystal" is defined as a multicomponent crystal of, at least, two molecules combined in a stoichiometric ratio in which one is the active API and the other the coformer, with the two molecules being connected through hydrogen bonding, van der Wall forces or π-stacking. The coformer can be another API or a pharmaceutical excipient, vitamin or amino acid.

The term "co-crystal purity" is defined as a measure of the conversion percentage, such that a conversion percentage of less than 100% means that other reagents (e.g. APIs and/or excipients) or other forms (e.g. amorphous forms) are present in the final product as impurities. For example a co-crystal purity of 75% means that 75% of the multi-component particles formed comprise the desired multicomponent crystal described in the above paragraph and 25% of the multi-component particles formed comprise impurities in the form of impurities such as APIs, excipients or amorphous forms.

In a preferred embodiment, the solvent and the anti-solvent are selected according to the solubility of the component, e.g. API, and, if applicable, the excipient or excipients of interest.

The term "solvent" according to the present invention is a solvent or mixture of solvents wherein the component, e.g. API, and, if applicable, the excipient or excipients of interest are soluble.

The term "anti-solvent" according to the present invention is a solvent or a mixture of solvents wherein the component, e.g. API, and, if applicable, the excipient or excipients of interest show a substantially lower solubility when compared with the "solvent". Preferably, the API and, if applicable, the excipient or excipients of interest are substantially insoluble or insoluble in the "anti-solvent". It may also be desirable to add a pH adjusting agent to the "anti-solvent" solution such as sodium hydroxide, hydrochloric acid, tris buffer or citrate, acetate, lactate, meglumine, or the like. It may also be desirable to adjust the temperature of the anti-solvent mixture.

In the context of solvents and anti-solvents, the term "soluble" means from 10 to 30 parts solvent is needed to dissolve 1 part solute, the term "substantially lower solubility" means from 100 to 1000 parts solvent is needed to dissolve 1 part solute, the term "substantially insoluble" means from 1000 to 10,000 parts solvent is needed to dissolve 1 part solute, and the term "insoluble" means more than 10,000 parts solvent is needed to dissolve 1 part solute. Furthermore, in these definitions, the terms "parts solvent" and "part solute" refer to the appropriate volume of solvent in milliliters per gram of solute.

In the case of multi-component particles, the term "excipient" can be any pharmaceutical compound such as polymers, surfactants, surface modifiers, sugars, amino acids.

The first solution used in the method of the present invention may comprise at least one API, or it may comprise zero, one or more than one excipients, or, it may comprise at least one API and zero, one or more than one excipients.

The second solution used in the method of the present invention may comprise at least one API, or it may comprise zero, one or more than one excipients, or, it may comprise at least one API and zero, one or more than one excipients.

Preferably, the solids concentration in the first and second solutions is in the range of, but not limited to, from about 1 to about 30% (w/w).

The term "microreaction" refers to a technology that involves physical and/or chemical reactions within microreactors, micromixers, microchannels or any other component comprised within the microfluidic field. The term "microfluidization" encompasses continuous fluid processing through these microchannels, involving high shear, cavitation and uniform mixing in the meso- and micromixing range.

Preferably, in the case of multi-component particles, the proportion of at least one API to one or more than one excipient ranges from 95 to 5% (w/w) to 5 to 95% (w/w).

The first and second solution may comprise anionic surfactants, cationic surfactants or nonionic surfactants. Preferably, the term "surfactant" is used to describe a chemical compound that lowers the surface tension (or interfacial tension) between two liquids or between a liquid and a solid, hence surfactants are also known as surface modifiers. Surfactants may act as detergents, wetting agents, emulsifiers, foaming agents, and/or dispersants.

A diagram of the method of the present invention is shown in FIG. 1.

In a preferred embodiment of the mixing/precipitation step, the mixing occurs under controlled conditions using a microreactor (21) to produce a suspension. The microreactor facilitates highly effective molecular contact/interaction within a defined reaction chamber or micro channels to form a suspension (12) by precipitation or co-precipitation of the substances in the two solutions.

The solutions may be continuously pumped into the reaction chamber where they are mixed and allowed to react.

Preferably, the reaction chamber comprises one or more channels of well-defined diameter and size. Preferably, the diameter of the channels is in the range of about 10 microns to about 400 microns. More preferably, the diameter is in the range of about 50 microns to about 200 microns. In embodiments using more than one microreactor, the microreactors may be arranged in series or in parallel.

The solutions are continuously pumped into the reaction chamber where they are mixed and allowed to react (continuous flow reaction). The microreactor (21) may be a continuous flow reactor.

The first solution (11) and second solution (10) are fed to one or more intensifier pumps (20) at individually controlled rates. The interaction between the components present in the first and second solutions is substantially prevented prior to pressurization with the intensifier pumps, controlling for example, mixing ratios, and process pressure.

The ratio of anti-solvent to solvent is dependent on the characteristics of the solvents and the components present in the first and second solutions, such as supersaturation capacity of the solvents and precipitation rates of the components. The ratio should be optimized to control particle characteristics (e.g. particle size, density, morphology, polymorphic form, crystallinity, etc.). In a preferred embodiment, the ratio of anti-solvent to solvent can vary from between 1:1 to 40:1, optionally from between 1:1 to 1:25.

Then, the first solution (11) and the second solution (10) are pressurized in a combined stream with the one or more intensifier pumps (20) to the microreactor (21), causing the components present in the first and second solutions to interact within the microreactor at a nano-scale level. The selection of mixing ratio, process pressure and solids concentration should be optimized to achieve the desired particle size.

The first solution may be combined with the second solution at a pressure sufficient to cause interaction of the at least one component, at least one solvent, at least one anti-solvent and any additional reagents present in the solutions; and delivered to one or more channels in a microreactor such that the at least one component, at least one solvent, at least one anti-solvent and any additional reagents present in the solutions react to form a suspension of amorphous particles by precipitation or co-precipitation.

The pressure may be in the range of from about 1 bar to about 3500 bar, optionally from about 20 to about 3500 bar, from about 100 to about 3000 bar, or from about 300 bar to about 2500 bar.

In the next step the suspension (12) is fed to a filtration system (22) to increase the solids concentration and obtain a concentrate stream (14). A pump can be used to transport the suspension from the at least one microreactor to the filtration system. Preferably, the filtration system (22) comprises a tangential flow filtration system, a cross-flow filtration system or any similar system known by those skilled in the art that enables the continuous concentration of a suspension by filtration, microfiltration, ultrafiltration, diafiltration or nanofiltration. In embodiments in which the filtration system comprises at least one cross-flow membrane system, the pore size of the membrane ranges from about 1 nm to about 100 microns, preferably, from about 10 nm to about 1 micron. The at least one cross-flow membrane system can comprise a cross-flow flat sheet membrane, a cross-flow tubular membrane, a cross-flow spiral membrane, a cross-flow hollow fiber membrane, and/or a cross-flow cassette membrane. Preferably, the membrane is a cross-flow cassette membrane. The at least one cross-flow membrane system can comprise an inorganic microsieve type cross-flow membrane or a polymeric track-etched cross-flow membrane. The membranes used on the selected system should be selected to minimize the product loss. One or more filtration systems, for example multiple tangential flow filtration systems, may be used in series or in parallel.

Preferably, an optional buffer tank is used to discharge the suspension (12) after the microreactor (21). In embodiments including a buffer tank.

Preferably, an optional pump is used to transport the suspension from the optional buffer tank to the filtration system (22).

The permeate stream (13) is mainly product-free and consequently discarded.

Preferably, a second optional buffer tank is used to discharge the concentrate stream (14) after the filtration system (22). A portion of the concentrate stream (14) can be optionally recirculated to the filtration system (22).

A pump can be used to transport the concentrate stream (14) to an atomizer. The feed rate helps determine the drying rate of the droplets, and therefore should be adjusted depending on the composition of concentrate stream (14).

Atomization can be promoted using specific types of nozzle such as, but not limited to, rotary type nozzles, pressure nozzles, two fluid nozzles or ultrasonic nozzles. The atomization helps to avoid aggregation of the particles and preferred atomization conditions promote very small droplets.

The drying of the spray can be performed in a drying chamber (23) and can be promoted by a drying gas stream (15). The stream of gas may be co-current or counter-current with respect to the atomized concentrate stream direction. The stream of gas may comprise nitrogen, air, carbon dioxide or combinations thereof. The temperature of the inlet gas helps to determine the drying rate of the droplets, and therefore should be adjusted depending on the composition of concentrate stream (14).

In a preferred embodiment, a high efficiency cyclone (24) may be used to collect the micro- and/or nanoparticles produced and/or the micro- and/or nanoparticles may be collected using filters.

The method of the present invention may further comprise the step of cooling or quenching the combined streams after interaction within the microreactor (21). The combined streams may be cooled or quenched by any method known in the art such as, but not limited to, methods using a heat exchanger or a quenching tower.

An organic compound for use as the at least one component in the method of the present invention may be any organic chemical entity whose solubility decreases from one solvent to another. This organic compound is preferably one or more APIs. Examples of preferred APIs include, but are not limited to, poorly soluble active compounds, thermolabile compounds with poor stability, or APIs requiring small particle size and high densities.

In the context of the at least one component, the definition of "low solubility", "poorly soluble" and "poorly water soluble" compounds corresponds to that of the Biopharmaceutics Classification System (BCS). According to the BCS, compounds can be divided in four classes, regarding solubility (according to the United States Pharmacopeia) and intestinal permeability. Class I compounds possess high permeability and high solubility, Class II compounds possess high permeability and low solubility, Class III compounds are characterized by low permeability and high solubility and Class IV compounds possess low permeability and low solubility. Poorly soluble compounds correspond to Class II and Class IV.

Examples of poorly soluble compounds include, but are not limited to: antifungal agents like intraconazole or a related drug, such as fluoconazole, terconazole, ketoconazole and saperconazole; anti-infective drugs, such as griseofulvin and related compounds (e.g. griseoverdin); anti malaria drugs (e.g. Atovaquone); protein kinase inhibitors such as Afatinib, Axitinib, Bosutinib, Cetuximab, Crizotinib, Dasatinib, Erlotinib, Fostamatinib, Gefitinib, Ibrutinib, Imatinib, Zemurasenib, Lapatinib, Lenvatinib, Mubritinib or Nilotinib; immune system modulators (e.g. cyclosporine); cardiovascular drugs (e.g. digoxin and spironolactone); ibuprofen; sterols or steroids; drugs from the group comprising danazol, acyclovir, dapsone, indinavir, nifedipine, nitrofurantion, phentytoin, ritonavir, saquinavir, sulfamethoxazole, valproic acid, trimethoprin, acetazolamide, azathioprine, iopanoic acid, nalidixic acid, nevirapine, praziquantel, rifampicin, albendazole, amitrptyline, artemether, lumefantrine, chloropromazine, ciprofloxacin, clofazimine, efavirenz, iopinavir, folic acid, glibenclamide, haloperidol, ivermectin, mebendazole, niclosamide, pyrantel, pyrimethamine, retinol vitamin, sulfadiazine, sulfasalazine, triclabendazole, and cinnarizine.

A detailed listing of groups of preferred poorly soluble compounds includes, but is not limited to: active agents or bioactive compounds of the group of ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective α2-adrenergic agonists, analgesics, antipyretics and anti-inflammatory agents, androgens, anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretics, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinsons agents, antiplatelet agents, antiprogestins, antithyroid agents, antitussives, antiviral agents, antidepressants, azaspirodecanediones, barbituates, benzodiazepines, benzothiadiazides, beta-adrenergic agonists, beta-adrenergic antagonists, selective β1-adrenergic antagonists, selective β2-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, haematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like, alone or in combination.

Preferred examples of the pharmaceutically active compound include, but are not limited to, fluticasone propionate and carbamazepine.

The solvent used in the method, according to the present invention, is preferably a solvent or mixture of solvents in which the at least one component, preferably APIs, are at least partially soluble.

Examples of such solvents include, but are not limited to: water, acetone, methylchloride, dimethylformamide, methanol, ethanoldimethyl sulfoxide, methylethylketone, dimethylacetamide, lactic acid, isopropanol, 3-pentanol, n-propanol, glycerol, butylene glycol, ethylene glycol, propylene glycol, dimethyl isosorbide, tetrahydrofuran, 1,4-dioxanepolyethylene glycol, polyethylene glycol esters, polyethylene glycol sorbitans, polyethylene glycol monoalkyl ethers, polypropylene glycol, polypropylene alginate, butanediol or mixtures thereof.

The anti-solvent, according to the present invention, may be miscible or immiscible with the solvent in the first solution and the at least one API and one or more than one excipients that may be present in the first solution show low solubility or completely insolubility upon mixing. The preferred anti-solvent is, but not exclusively, an aqueous solution.

Polymers suitable for use in the present invention include, but are not limited to, cellulose ester, cellulose ether, polyalkylene oxide, polyacrylate, polymethacrylate, polyacrylamide, polyvinyl alcohol, vinyl acetate polymer, oligosaccharide, polysaccharide, hydroxypropylcellulose, polyvinylpyrrolidone, hydroxyalkylcelluloses, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, hydroxypropylmethylcellulose succinate, butyl methacrylate/2-dimethylaminoethyl methacrylate copolymer, poly(hydroxyalkyl acrylate), poly(hydroxyalkyl methacrylate), gelatin, copolymer of vinyl acetate and crotonic acid, partially hydrolyzed polyvinyl acetate, carrageenan, galactomannan, high viscosity gums or xanthan gum, or a combination thereof.

Examples of other excipients include those having at least one functional group selected from: thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, imine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine.

Particles obtainable by the method of the present invention include single component particles, multi-component particles, particulate amorphous solid dispersions and particulate co-crystals and may have a particle size ranging from nano-range to micro-range. These particles may comprise from about 5 to about 100% (w/w), optionally from about 5 to about 95% (w/w), of at least one API and from about 95 to about 5% (w/w) of one or more than one excipient and/or may have a bulk density in the range of from about 0.1 g/ml to about 1.0 g/ml. The single component particles, multi-component particles, particulate amorphous solid dispersions and particulate co-crystals may be formulated into pharmaceutical compositions and may be used as a medicament.

Single component particles and multi-component particles obtainable by the method of the present invention may comprise 0% of a surfactant or greater than 0% surfactant. The particle size of the single component particles and multi-component particles can range from about 50 nm to about 10 µm, optionally from about 50 nm to about 2 µm, from about 50 nm to about 1 µm, or from about 50 nm to about 800 nm. The single component particles or multi-component particles may be used to increase the bioavailability of an API, such as carbamazepine.

The particle size of the particulate amorphous solid dispersions obtainable by the method of the present invention can range from about 50 nm to about 1 µm, optionally from about 50 nm to about 800 nm. The particulate amorphous solid dispersion may be used to increase the bioavailability of an API. Examples of pharmaceutical forms for administration of amorphous solid dispersions synthesized according to the method of the present invention may include solid dosage forms, such as tablets, capsules, granules, pellets or powders. The compositions obtained may have an enhanced performance including, but not exclusively, supersaturation, bioavailability, dissolution rate improvement, controlled release or taste masking.

The particle size of the particulate co-crystals obtainable by the method of the present invention can range from about 50 nm to about 10 µm, optionally from about 50 nm to about 2 µm. The co-crystal purity can be at least 50% (w/w), optionally at least 75% (w/w), or at least 90% (w/w). The particulate co-crystals may be used to increase the aqueous solubility, bioavailability, hygroscopicity, stability and/or taste of an API.

The skilled person seeking to prepare either a particulate amorphous solid dispersion or a particulate co-crystal would select excipients that enable either the formation of a dispersion of at least one API in a matrix or a multicomponent crystal of at least two molecules combined in a stoichiometric ratio in which one is the active API and the other the coformer, as described above. For example, the skilled person seeking to prepare a particulate co-crystal, would select excipients that have a favourable intermolecular interaction with the API, promoting hydrogen bonding, van der Wall forces or π-stacking. In addition, the skilled person could adjust the ratio of solvent to anti-solvent and the concentrations of the first and second solutions to help produce the desired products.

EXAMPLES

Example 1

Carbamazepine (3.19 g) and saccharin (2.47 g) were dissolved in a molar proportion 1:1 in methanol (119 g). Deionized water was used as the anti-solvent. A mass of deionized water corresponding to two times the mass of the solvent was measured.

Co-precipitation of co-crystals was performed using a micro-fluidizer reactor processor (Microfluidics, Model MRT CR5) comprising a chamber with 75 µm diameter reaction channels followed by an auxiliary processing module with 200 µm diameter reaction channels. The peristaltic pump was set to maintain a ratio of 1:2 of solvent and anti-solvent. The intensifying pump was set to impose a pressure of 1379 bar.

Figure 2:
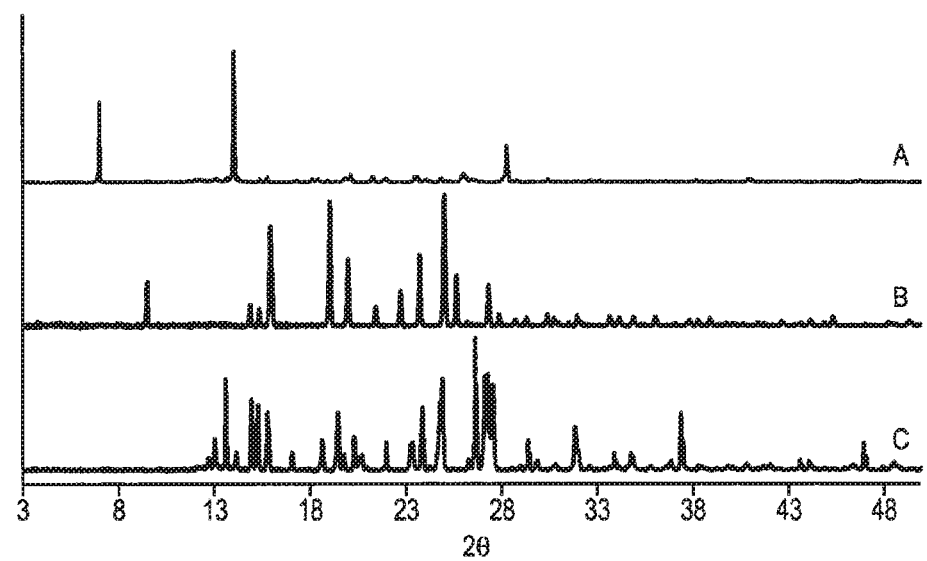
FIG. 2 shows the XRPD patterns and normalized intensity (I) of A) carbamazepine-saccharin co-crystals, B) saccharin, C) carbamazepine.

The resulting suspension was fed to a cross-flow filter with a membrane pore of 0.47 µm. The suspension was also analyzed by X-ray powder diffraction (XRPD) characterization and presented the target crystalline form of carbamazepine-saccharin co-crystals as described by Porter III et al. (*Crystal Growth & Design*, 2008, 8, 14-16). FIG. 2 shows the XRPD analysis of the co-crystals and the corresponding raw materials. The obtained product had the same target crystalline form of carbamazepine-saccharin co-crystal that was obtained before drying.

Figure 3:
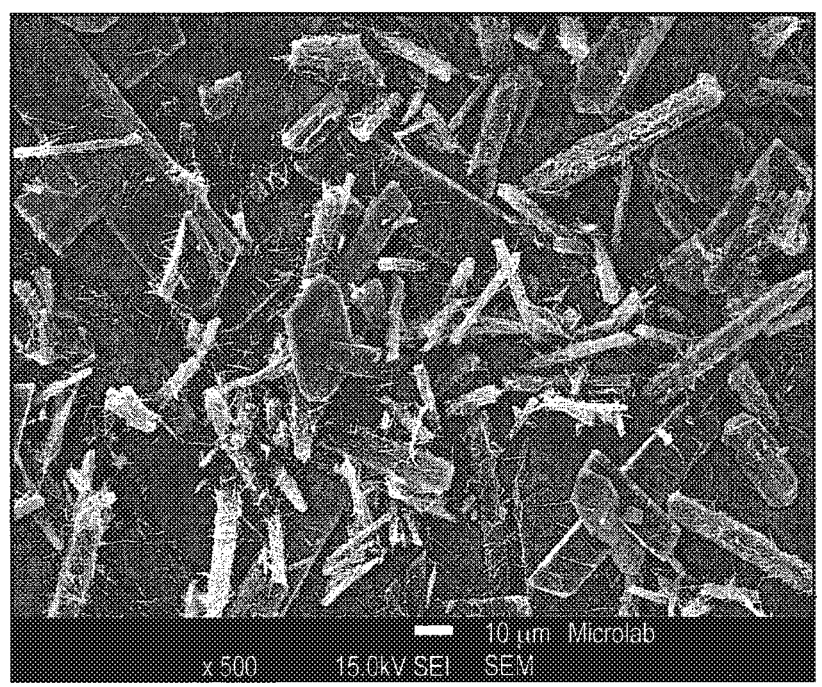
FIG. 3 shows a SEM image of carbamazepine-saccharin co-crystal particles produced in accordance with one embodiment of the method of the present invention.

The isolated product was characterized by scanning electron microscopy (SEM) for particle size determination. A representative image of the particles is shown in FIG. 3.

Example 2

Fluticasone propionate (6 g) was dissolved in acetone (476 g). Deionized water was used as the anti-solvent. A mass of deionized water corresponding to ten times the mass of the solvent was measured.

Figure 4:
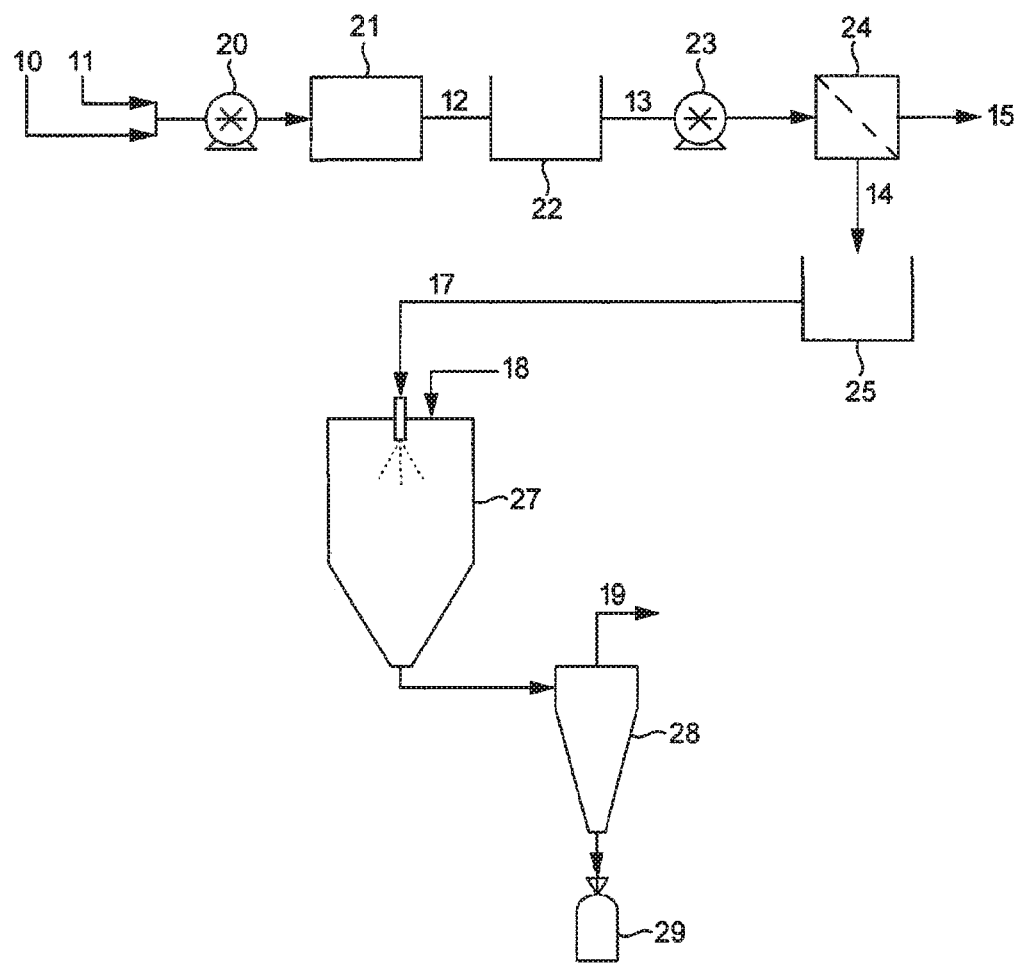
FIG. 4 is a diagram of one embodiment of the method of the present invention comprising a pump to feed the produced suspension to the filtration system.

FIG. 4 is a diagram of one embodiment of the method of the present invention, which embodiment was used in this example. In this embodiment a pump is used to feed the suspension to the filtration system.

The precipitation in the form of API particles was performed using a micro-fluidizer reactor processor (Microfluidics, Model MRT CR5) comprising a chamber with 75 µm diameter reaction channels followed by an auxiliary processing module with 200 µm diameter reaction channels. The peristaltic pump was set to maintain a ratio of 1:10 of solvent (10) and anti-solvent (11). The intensifying pump (20) was set to impose a pressure of 1379 bar.

The resulting suspension was continuously fed to a buffer tank (22) under agitation at a flowrate of 560 mL/min. The buffer tank (22) level was maintained constant during operation. The buffer tank outlet was continuously fed by a pump (23) at a flowrate 50 mL/min the Cogent M1 tangential flow filtration system (24) comprising one Pellicon cassette with a pore size of 0.22 µm and a filtration area of 0.1 m² to obtain the concentrate. The concentrate (14) was continuously supplied to a second buffer tank (25) under agitation. The second buffer tank (25) level was maintained constant during operation. The buffer tank outlet (17) was continuously fed to a laboratory scale spray dryer (27) (Büchi, model B-290) using a peristaltic pump (not shown in the Figure). The laboratory scale spray dryer (27) was equipped with a two fluid nozzle in order to atomize and dry the suspension (17). Co-current nitrogen (18) was used to promote the drying after atomization. The spray dryer (27) was operated in open cycle mode (i.e., without recirculation of the drying gas) with a feed rate of 10 mL/min and a drying temperature of 80° C.

Figure 5:
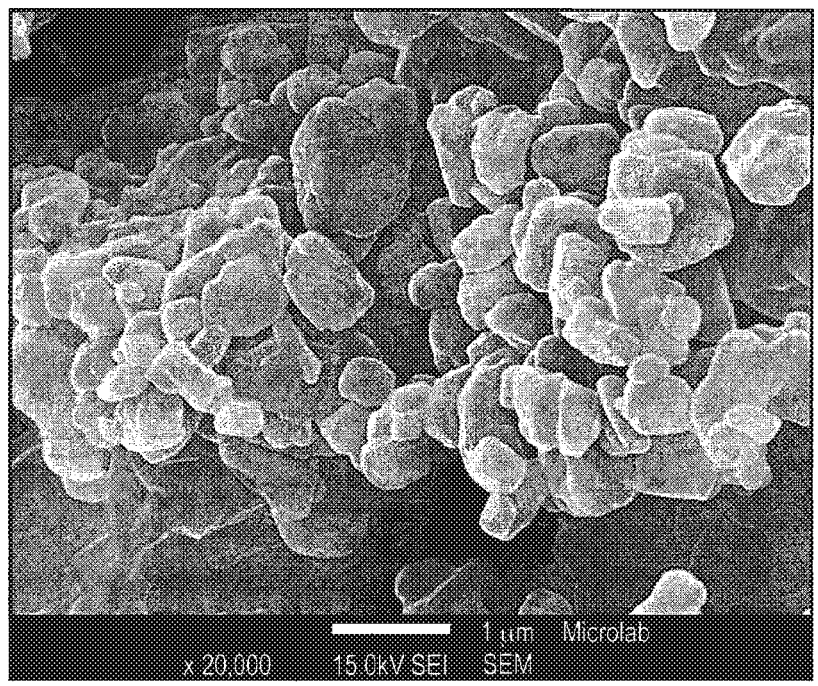
FIG. 5 shows SEM images of fluticasone propionate particles produced in accordance with one embodiment of the method of the present invention (ContinuousA-A), fluticasone propionate particles produced by a batch process of co-precipitation followed by spray drying (BatchB-B) and fluticasone propionate particles stabilized with a surfactant produced by a batch process of co-precipitation followed by spray drying (BatchC-C)
Figure 5:
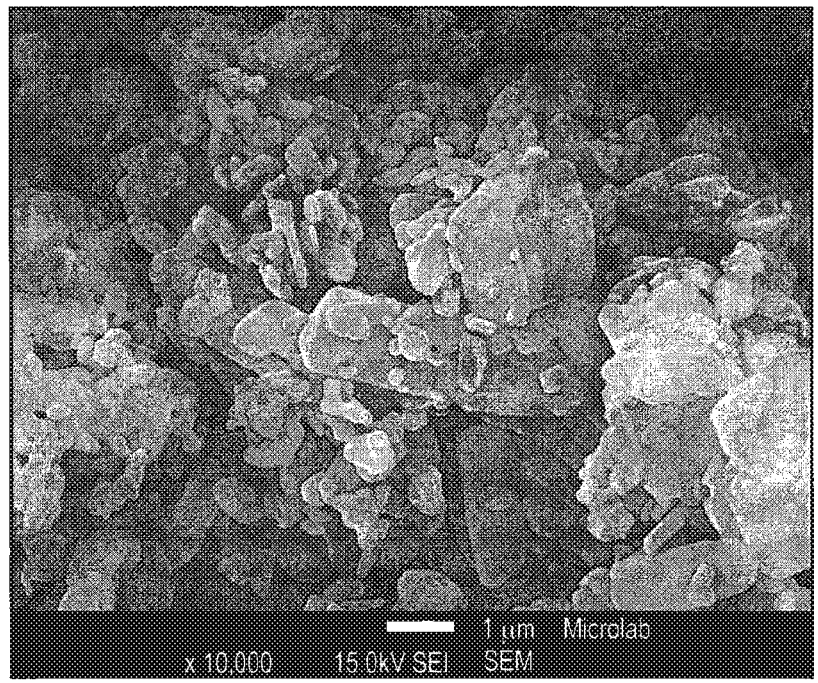
Figure 5:
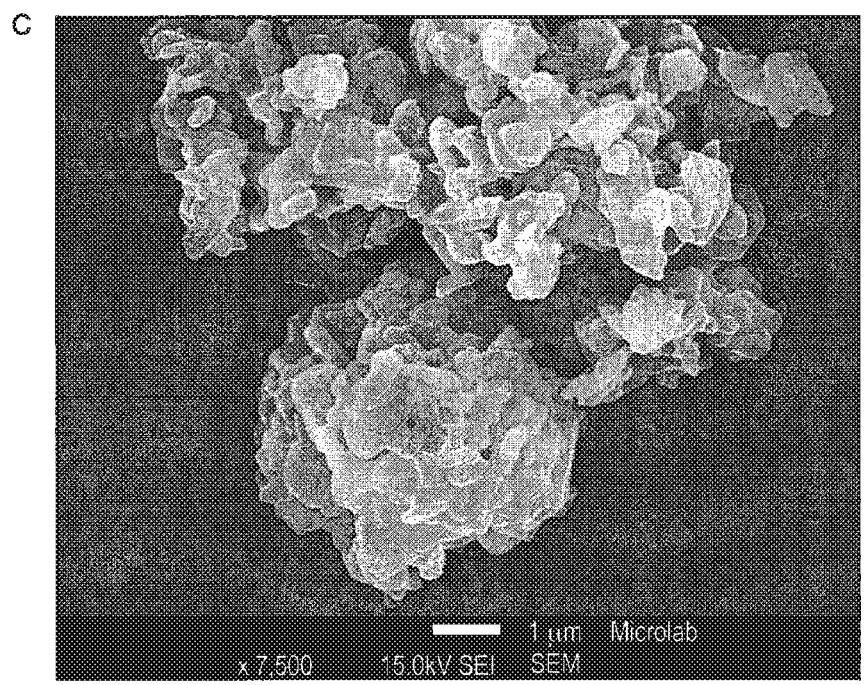

The isolated product (ContinuousA) was characterized by SEM for particle size determination. A representative image of the particles is shown in FIG. 5 (ContinuousA-A).

For comparison purposes, two other trials (BatchB and BatchC) were conducted using microreaction technology followed by spray drying. Concerning BatchB, the conditions on solution preparation and further precipitation were similar to ContinuousA production, but the suspension stream (12) was collected in a vessel and supplied under agitation to a spray dryer unit in the same conditions as for ContinuousA. Concerning BatchC, fluticasone propionate (3 g) and Poloxamer 188 (3 g), a surfactant, were dissolved in acetone (476 g). The precipitation and drying method were performed as for BatchB. The particle size of the isolated products was characterized by SEM. As presented in FIG. 5, micro- and nano-size particles with a wide particle size distribution were obtained with BatchB. This wide particle size distribution may be explained by the long drying time, and consequently aging time, of the suspension produced. Concerning BatchC, the particles have a similar size, but with a narrow particle size distribution due to the addition of surfactant in the formulation. The surfactant is able to prevent Oswald Ripening phenomena during the drying time of the suspension. Finally, the ContinuousA particles have as narrow a particle size distribution as BatchC, but without any surfactant addiction. This narrow particle size distribution may be explained by the short residence time of the suspension in the continuous method used in ContinuousA production.

Example 3

Fluticasone propionate (6 g) was dissolved in acetone (476 g). Deionized water was used as the anti-solvent. A mass of deionized water corresponding to ten times the mass of the solvent was measured.

Figure 6:
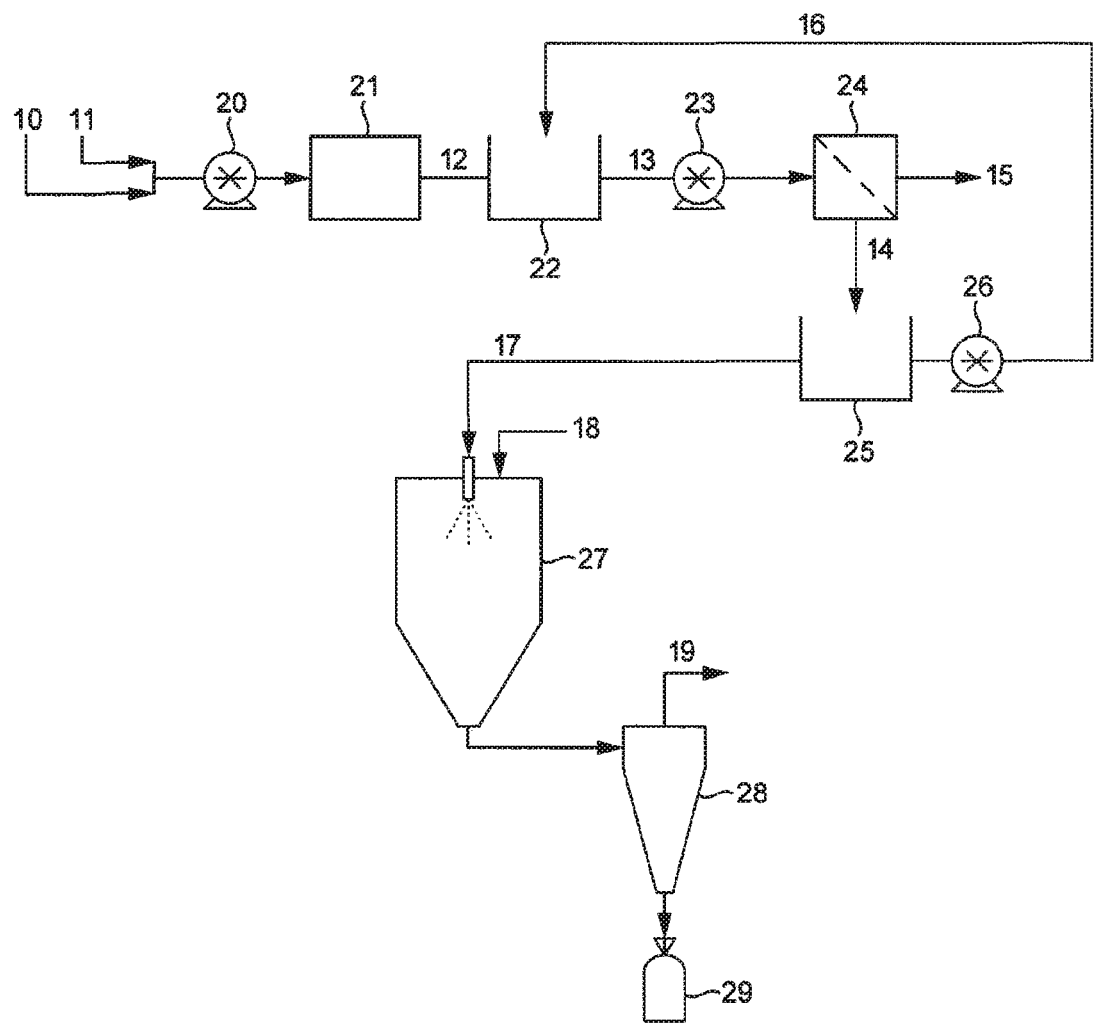
FIG. 6 is a diagram of one embodiment of the method of the present invention comprising a pump to feed the produced suspension to the filtration system and a recirculation stream.

FIG. 6 is a diagram of one embodiment of the present invention, which embodiment was used in this example. In this embodiment a pump is used to feed the suspension to the filtration system.

The precipitation in the form of API particles was performed using a micro-fluidizer reactor processor (Microfluidics Model MRT CR5) comprising a chamber with 75 µm diameter reaction channels followed by an auxiliary processing module with 200 µm diameter reaction channels. The peristaltic pump (not shown in the Figure) was set to maintain a ratio of 1:10 of solvent (11) and anti-solvent (10). The intensifying pump (20) was set to impose a pressure of 1379 bar.

The resulting suspension was continuously fed to a buffer tank (22) under agitation at a flowrate of 560 mL/min. The buffer tank (22) level was maintained constant during operation. The buffer tank outlet (13) was continuously fed the Cogent M1 tangential flow filtration system comprising one Pellicon cassette (24) with a pore size of 0.22 µm and a filtration area of 0.1 m$^2$ using a pump (23) at a flowrate of 52 mL/min to obtain the concentrate (14). The said concentrate was continuously supplied to a second buffer tank (25) under agitation. The second buffer tank (25) level was maintained constant during operation. The second buffer tank (25) had two outlets: recirculate stream (16) at a flowrate of 42 mL/min which fed a tank (22) by pump (26), and other outlet stream (17) which fed a laboratory scale spray dryer (27) (Bëchi, model B-290) using a peristaltic pump (not shown in the Figure).

The laboratory spray dryer (27) was equipped with a two fluid nozzle in order to atomize and dry the suspension (17). Co-current nitrogen (18) was used to promote the drying after atomization. The spray dryer (27) was operated in open cycle mode (i.e., without recirculation of the drying gas) with a feed rate of 10 mL/min and a drying temperature of 80° C.

Figure 7:
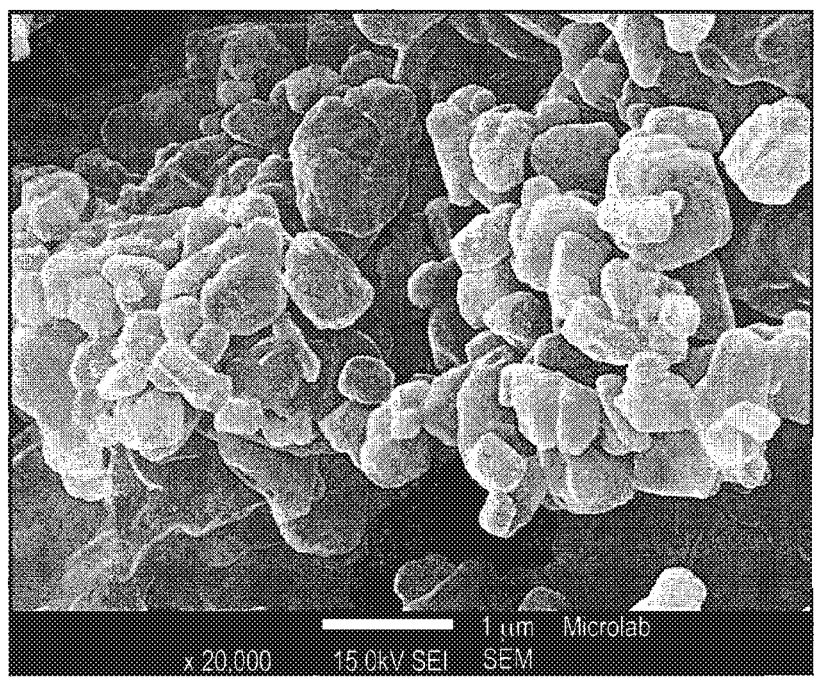
FIG. 7 is a SEM image of fluticasone propionate particles produced in accordance with one embodiment of the method of the present invention.

The isolated product was characterized by SEM for particle size determination. A representative image of the particles is shown in FIG. 7. Approximately micro- and nano-size particles were obtained. Comparing the particles obtained as shown in FIG. 7 to the particles of the ContinuousA product obtained in Example 3, as shown in FIG. 4A, it appears that the particle size was not affected by increasing the residence time due to the recirculation stream (16).

X-Ray Powder Diffraction (XRPD)

X-ray powder diffractograms were obtained in a D8 Advance Bruker AXS Theta-2Theta diffractometer with a copper radiation source (Cu Kα2, λ=1.5406 Å), voltage of 40 kV, and filament emission of 35 mA. For the total scan, the samples were measured over a 2θ interval from 3 to 70° with a step size of 0.017° and step time of 50 s.

Scanning Electron Microscopy (SEM)

The samples were attached to adhesive carbon tapes (Ted Pella Inc., CA, USA), previously fixed to aluminum stubs where the powder in excess was removed by a jet of pressurized air. The samples were left under vacuum for 2 hours and then coated with gold/palladium (South Bay Technologies, model E5100, San Clement, Calif.). A JEOL JSM-7001F/Oxford INCA Energy 250/HKL scanning electron microscope (JEOL, Japan) operated in high vacuum at an accelerating voltage of 15 kV was used.

The invention claimed is:

1. A method of continuously manufacturing single component particles or multi-component particles, which method comprises the steps of:
   preparing a first solution comprising at least one component and at least one solvent, and a second solution comprising at least one anti-solvent of the at least one component comprised in the first solution, wherein the second solution further comprises (1) at least one API, (2) at least one excipient, or (3) a combination of at least one API and at least one excipient;
   continuously feeding said first solution and said second solution to at least one microreactor having a reaction chamber to obtain a first suspension containing particles and the substances in the two solutions by precipitation or co-precipitation of the substances in the two solutions;
   continuously feeding said first suspension to a filtration system to obtain a concentrate stream, wherein the concentrate stream is a second suspension containing the particles and the substances in the two solutions;
   continuously feeding said concentrate stream directly to a spray dryer;
   atomizing said concentrate stream using at least one atomization nozzle;
   drying said atomized concentrate stream to obtain the particles; and
   collecting said particles.

2. The method according to claim 1, wherein the first solution comprises (i) at least one active pharmaceutical ingredient (API); (ii) one or more than one excipient; or (iii) both (i) and (ii).

3. The method according to claim 1, wherein the at least one microreactor comprises at least one of the following features:
   (i) the at least one microreactor comprises one or more channels each having a diameter in the range of 10 micrometers to 400 micrometers;
   (ii) the at least one microreactor comprises more than one microreactor, arranged in series or in parallel;
   (iii) the at least one microreactor is a continuous flow reactor.

4. The method according to claim 1, wherein the first solution is combined with the second solution at a pressure sufficient to cause interaction of the at least one component, at least one solvent, at least one anti-solvent and any additional reagents present in the solutions; and delivered to one or more channels in a microreactor such that the at least one component, at least one solvent, at least one anti-solvent and any additional reagents present in the solutions react to form a suspension of particles by precipitation or co-precipitation, and wherein the pressure is in the range of from 1 bar (0.1 MPa) to 3500 bar (350 MPa).

5. The method according to claim 1, further comprising cooling or quenching the suspension after the solutions have mixed within the at least one chamber.

6. The method according to claim 1, wherein a pump is used to transport the suspension from the at least one chamber to the filtration system.

7. The method according to claim 1, wherein the filtration system comprises at least one tangential flow filtration system or at least one cross-flow membrane system; and wherein, when the filtration system comprises at least one cross-flow membrane system, the pore size of the membrane in the at least one cross-flow membrane system ranges from 1 nm to 100 micrometer.

8. The method according to claim 7, wherein the filtration system comprises at least one cross-flow membrane system; wherein the at least one cross-flow membrane system comprises a cross-flow flat sheet membrane, a cross-flow tubular membrane, a cross-flow spiral membrane, a cross-flow hollow fiber membrane, a cross-flow cassette membrane, or combinations thereof; and wherein the at least one cross-flow membrane system comprises an inorganic microsieve type cross-flow membrane or a polymeric track-etched type cross-flow membrane.

9. The method according to claim 7, wherein the tangential flow filtration systems or cross-flow membrane systems are arranged in series or in parallel.

10. The method according to claim 1, wherein the at least one atomization nozzle comprises a rotary type nozzle, a pressure nozzle, a fluid nozzle, or an ultrasonic nozzle.

11. The method according to claim 1, wherein drying is promoted by a gas stream, optionally wherein the gas stream is co-current or counter-current with respect to the atomized concentrate stream direction and/or the gas stream comprises nitrogen, air, carbon dioxide or a combination thereof.

12. Particles obtainable according to claim 1, wherein the particles are in the form of (i) single component particles or multi-component particles; (ii) a particulate amorphous solid dispersion; or (iii) a particulate co-crystal.

13. Single component particles, multi-component particles, a particulate amorphous solid dispersion or a particulate co-crystal according to claim 12, wherein (i) the particles, (ii) the amorphous solid dispersion, or (iii) the particulate co-crystal comprise from 5 to 100% (w/w) of at least one API and from 95 to 0% (w/w) of one or more than one excipient.

14. Single component particles or multi-component particles according to claim 12, wherein the product comprises greater than 0% surfactant.

15. Single component particles, multi-component particles or a particulate amorphous solid dispersion or a particulate co-crystal according to claim 12, wherein the particles have a particle size ranging from nano-range to micro-range, and, in the case of single component particles, multi-component particles or a particulate amorphous solid dispersion, in the range of from 50 nm to 1 μm.

16. Single component particles, multi-component particles or a particulate amorphous solid dispersion or a particulate co-crystal according to claim 12, wherein the particles have a bulk density in the range of from 0.1 g/ml to 1.0 g/ml.

17. Single component particles, multi-component particles or a particulate amorphous solid dispersion according to claim 12, for use in increasing the bioavailability of an API or a particulate co-crystal according to claim 12, for use in increasing the aqueous solubility, bioavailability, hygroscopicity, stability and/or taste of an API.

18. Single component particles or multi-component particles according to claim 12, wherein the particles comprise fluticasone propionate.

19. A pharmaceutical composition comprising (i) single component particles or multi-component particles, (ii) a particulate amorphous solid dispersion, or (iii) a particulate co-crystal according to claim 12, optionally for use as a medicament.

20. The particulate co-crystal according to claim 12, wherein the co-crystal purity is at least 50% (w/w).

21. A method of continuously manufacturing single component particles or multi-component particles, which method comprises the steps of:
  preparing a first solution comprising at least one component and at least one solvent, and a second solution comprising at least one anti-solvent of the at least one component comprised in the first solution, wherein the second solution further comprises (1) at least one API, (2) at least one excipient, or (3) a combination of at least one API and at least one excipient;
  continuously feeding said first solution and said second solution to at least one microreactor having a reaction chamber to obtain a first suspension containing particles and the substances of the two solutions by precipitation or co-precipitation of the substances in the two solutions;
  continuously feeding said first suspension to a filtration system to obtain a concentrate stream, wherein the concentrate stream is a second suspension containing the particles and the substances in the two solutions;
  continuously feeding said concentrate stream directly to a spray dryer via a buffer tank;
  atomizing said concentrate stream using at least one atomization nozzle;
  drying said atomized concentrate stream to obtain the particles; and
  collecting said particles.

22. Single component particles or multi-component particles according to claim 12, wherein the product comprises 0% of a surfactant.

23. Single component particles, multi-component particles or a particulate amorphous solid dispersion or a particulate co-crystal according to claim 12, wherein the particles have a particle size in a range of from 50 nm to 10 μm and, in the case of single component particles, multi-component particles or a particulate amorphous solid dispersion, in a range of from 50 nm to 1 μm.

* * * * *